United States Patent
Belden

(10) Patent No.: US 7,580,811 B2
(45) Date of Patent: Aug. 25, 2009

(54) MEDICAL DATA COMMUNICATION INTERFACE MONITORING SYSTEM

(75) Inventor: Alvin Belden, Ardmore, PA (US)

(73) Assignee: Siemens Medical Solutions Health Services Corporation, Malvern, PA (US)

( * ) Notice: Subject to any disclaimer, the term of this patent is extended or adjusted under 35 U.S.C. 154(b) by 526 days.

(21) Appl. No.: 11/386,965

(22) Filed: Mar. 22, 2006

(65) Prior Publication Data

US 2007/0043535 A1   Feb. 22, 2007

Related U.S. Application Data

(60) Provisional application No. 60/667,545, filed on Apr. 1, 2005.

(51) Int. Cl.
*G21C 17/00* (2006.01)
*G06F 11/30* (2006.01)

(52) U.S. Cl. .................. 702/182; 702/176; 702/183; 710/107

(58) Field of Classification Search .................. 702/127, 702/176, 179, 183, 185; 370/241, 419, 420; 707/102; 709/223, 224, 227; 715/736; 710/107; 714/48

See application file for complete search history.

(56) References Cited

U.S. PATENT DOCUMENTS

| 5,835,735 | A * | 11/1998 | Mason et al. ............... 710/107 |
| 6,381,557 | B1 * | 4/2002 | Babula et al. ............... 702/183 |
| 6,658,367 | B2 * | 12/2003 | Conrad ....................... 702/176 |
| 2004/0122702 | A1 | 6/2004 | Sabol et al. |
| 2005/0063575 | A1 | 3/2005 | Ma et al. |
| 2005/0158767 | A1 | 7/2005 | Haskell et al. |
| 2005/0182846 | A1 | 8/2005 | Schofield et al. |
| 2005/0196030 | A1 | 9/2005 | Schofield et al. |

* cited by examiner

*Primary Examiner*—John H. Le
(74) *Attorney, Agent, or Firm*—Alexander J. Burke

(57) ABSTRACT

A system maintains statistics on DICOM interfaces that include for each interfaced Application Entity, the number, timing and types of DICOM failures, number and timing of broken network connections, number and types of transactions and time required to perform each transaction, in the determination of a level of communication performance within individual interface applications. A system monitors performance of a communication interface supporting communication of patient medical data. The system includes an acquisition unit for acquiring performance related data concerning operation of a particular interface supporting communication of patient medical data. A data processor processes the acquired interface performance related data to provide a statistical measure including an interface performance parameter value and compares the performance parameter value with a predetermined threshold value to determine if interface performance is below a predetermined level. A result processor automatically initiates corrective action to improve operation of the particular interface in response to a determination the interface performance is below the predetermined level.

17 Claims, 3 Drawing Sheets

MEDICAL DATA COMMUNICATION INTERFACE MONITORING SYSTEM

This is a non-provisional application of provisional application Ser. No. 60/667,545 by A. Belden filed Apr. 1, 2005.

FIELD OF THE INVENTION

This invention concerns a system for monitoring and improving performance of a communication interface supporting communication of patient medical data.

BACKGROUND OF THE INVENTION

A data communication interface (e.g., a DICOM protocol compatible interface) used in communicating medical data (such as a DICOM compatible Service-Object Pair (SOP) Class may experience degraded performance or intermittently fail without a site administrator being aware of the condition. The DICOM protocol comprises the Digital Imaging and Communications in Medicine protocol standard (developed approximately 1990) and a DICOM Service-Object Pair describes a DICOM data object and associated service, such as a DICOM Store_CT-Image, store_MR-Image, Print CT-Image data object, for example. The absence of awareness of degraded performance by a site administrator results in sub-optimal system operation, dissatisfied employees and may potentially harm patients because data carried across DICOM interfaces is often vital to patient care. A DICOM MWL (Modality Worklist), for example, is used to transmit patient and procedure identifiers from a Radiology Information System to Acquisition Modalities e.g. CT scanner, MRI device, Ultrasound. If this information does not arrive in a timely manner to the device performing the medical procedure, manual entry of identifiers is typically employed which can result in misidentification of patients or procedures resulting in delayed or improper care. There are a myriad of other examples in which the failure of information to arrive in a timely manner may impair patient treatment. A system according to invention principles addresses these deficiencies and related problems.

SUMMARY OF THE INVENTION

A system statistically evaluates typical performance of individual communication (e.g., DICOM) interface applications and determines a level of communication performance within individual interface applications. A system monitors performance of a communication interface supporting communication of patient medical data. The system includes an acquisition unit for acquiring performance related data concerning operation of a particular interface supporting communication of patient medical data. A data processor processes the acquired interface performance related data to provide a statistical measure comprising an interface performance parameter value and compares the performance parameter value with a predetermined threshold value to determine if interface performance is below a predetermined level. A result processor automatically initiates corrective action to improve operation of the particular interface in response to a determination the interface performance is below the predetermined level.

DETAILED DESCRIPTION OF THE INVENTION

Figure 1:
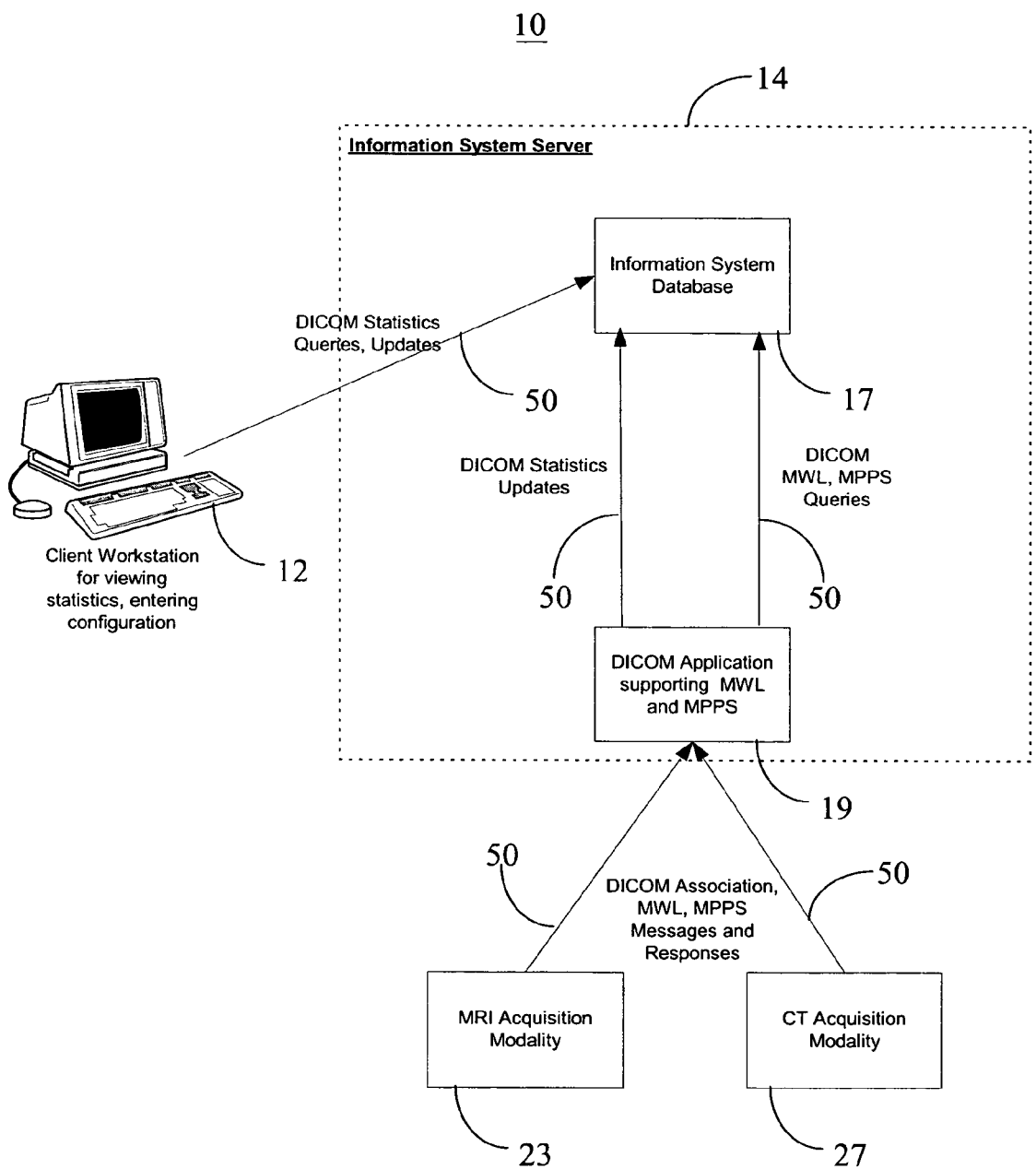
FIG. 1 shows a system for monitoring performance of a communication interface supporting communication of patient medical data, according to invention principles.

FIG. 1 shows system 10 for monitoring performance of a communication interface supporting communication of patient medical data. The system is used in conjunction with an Information System (e.g., a Radiology Information system (RIS) or a Picture Archiving Computer System (PACS)) and an image Acquisition Modality (e.g., an MRI, CT Scan, Ultrasound unit) and maintains statistics on a DICOM interface, for example. Statistics are maintained on individual interfaced Application Entities such as interface applications or peers. An image Modality Worklist (task list) function of a RIS employs an interface to individual acquisition modalities supporting the worklist function, for example. The system maintains statistics indicating number, timing and types of DICOM failures, number and timing of broken network connections, number and types of transactions and time required to perform each transaction.

A peer, as used herein, is an executable application operating on a given network node that participates in exchange of medical data according to a health communication protocol such as DICOM or HL7 with applications on other network nodes. A network node may be an image Acquisition Modality such as a CT (Computerized tomography) device, an Information System server, a workstation that is used to run PACS or RIS client software, etc. Peer is used interchangeably with interface application. An executable application as used herein comprises code or machine readable instruction for implementing predetermined functions including those of an operating system, healthcare information system or other information processing system, for example, in response user command or input. An executable procedure is a segment of code (machine readable instruction), sub-routine, or other distinct section of code or portion of an executable application for performing one or more particular processes and may include performing operations on received input parameters (or in response to received input parameters) and provide resulting output parameters.

A processor as used herein is a device and/or set of machine-readable instructions for performing tasks. A processor comprises any one or combination of, hardware, firmware, and/or software. A processor acts upon information by manipulating, analyzing, modifying, converting or transmitting information for use by an executable procedure or an information device, and/or by routing the information to an output device. A processor may use or comprise the capabilities of a controller or microprocessor, for example. A display processor or generator is a known element comprising electronic circuitry or software or a combination of both for generating display images or portions thereof. A user interface comprises one or more display images enabling user interaction with a processor or other device.

System 10 (FIG. 1) notifies on-site personnel via email or another means when a network communication interface application exceeds a specific failure rate or a given performance threshold. In addition, system 10 provides a user interface so that users can view statistics for individual network communication interface applications. The system may be incorporated in various applications that support DICOM communication interfaces, for example and be used as a self-diagnosing system that can notify users of problems. The system is usable by hospitals, clinics and other medical facilities employing Information Systems and image Acquisition Modalities supporting DICOM SOP Classes, for example and provides a capability to quickly identify problems in performance or failure of DICOM communication interfaces. A properly configured and operating DICOM interface provides substantially optimal network, database and CPU performance. However, there are performance costs (e.g., delay) associated with communication interfaces.

A DICOM SOP (Service-Object Pair) Class is the smallest piece of functionality within DICOM that can be conformed to or be supported. An example SOP Class is Modality Worklist. A user or a provider or both, may claim conformance to a SOP Class. A Radiology Information System typically claims conformance to a Modality Worklist SOP Class as a provider. Image Acquisition Modality devices claim conformance as users. A SOP Class is a scoping mechanism specifying a set of attributes, i.e., an object, and a type of message or service. In the case of a Modality Worklist the service is the C-FIND. Applications supporting Modality Worklist exchange C-FIND messages containing attributes specified for a Modality Worklist object (an Information Object Definition IOD). The service classes and information objects are combined to form the functional units of DICOM. This combination is called a service-object pair, or SOP.

A SOP class is the elemental unit of DICOM comprising data indicating both a service and an information object. For example, DICOM defines a series of storage SOP classes (e.g., CT image storage SOP class, MR image storage SOP class). The CT information object definition and the storage service class are combined to form the CT image storage SOP class. Other storage SOP classes are formed in a similar fashion. Because the SOP classes are referred to as a way to describe DICOM functionality, they carry Unique Identifiers (UIDs). Furthermore, once the attributes in the information object and the variables of the service class are "filled in" by values representing a real patient, a particular piece of imaging equipment, and a resulting image, the SOP class becomes a SOP instance and is assigned its own UID.

FIG. 1 illustrates flow of DICOM imaging Modality Worklist (MWL) messages and DICOM Modality Performed Procedure Step (MPPS) transactions in a hospital. The messages and transaction data passes from image Acquisition Modalities, specifically, MRI Acquisition modality 23 and CT Acquisition modality 27, to DICOM application 19 executing on a Radiology Information System server 14, for example. DICOM application 19 receives and processes the message and transaction data to provide statistics. The message and transaction data and derived statistics are provided to repository 17 for storage. Client device 12 (e.g., a workstation such as a PC, laptop, notebook, PDA or other processing device) accesses repository 17 to present statistical information for viewing and also enables a user to enter configuration data used in managing generation of statistics and processing data. Communication paths 50 (otherwise called network, bus, link, connection, channel, etc.) represent any type of protocol or data format not just DICOM protocol paths. The protocol or data format includes, but is not limited to, one or more of the following: an Internet Protocol (IP), a Transmission Control Protocol Internet protocol (TCPIP), a Hyper Text Transmission Protocol (HTTP), an RS232 protocol, an Ethernet protocol, a Medical Interface Bus (MIB) compatible protocol, a Local Area Network (LAN) protocol, a Wide Area Network (WAN) protocol, a Campus Area Network (CAN) protocol, a Metropolitan Area Network (MAN) protocol, a Home Area Network (HAN) protocol, an Institute of Electrical and Electronic Engineers (IEEE) bus compatible protocol, and a Health Level Seven (HL7) protocol. Communication paths 50 may comprise one or more paths in a network, foe example.

In operation, system 10 in response to imaging Modality device 23 or 27 sending a DICOM Modality Worklist query request for imaging task related information, application 19 acquires and stores data indicating, time of query, query keys (used in accessing data from a database) contained in the query request, number of responses returned and total time to process the query. System 10 employs a pre-configured rule stored in repository 17 or another repository accessible by application 19. The pre-configured rule initiates application 19 to notify a Radiology Information System Administrator once an hour of any Modality Worklist queries occurring in the previous hour that returned in excess of 200 responses or takes more than 30 seconds to process, for example. An additional pre-configured rule notifies the RIS Administrator once an hour if any Acquisition Modality has sent more than 30 queries in the past hour, for example. During a particular hour, MRI Acquisition Modality 23 sends forty Modality Worklist queries and generates an email to the RIS Administrator. The RIS Administrator receives the email and reconfigures the MRI unit to query less frequently, for example.

In existing systems, site administrators become aware of performance problems or intermittent failures in DICOM interfaces via sporadic complaints of users. Evidence of a problem may have disappeared by the time complaints are addressed. Existing implementations fail to comprehensively save DICOM statistics such as a number of images stored in conjunction with performance statistics or statistics per interfaced peer. This is of particular value for query services by which vendors can generate queries that return hundreds of responses. Such query services may be used to query every minute, for example, resulting in lowered network and database performance. Existing communication interface watchdog approaches monitor the state of individual services that are parts of a distributed application such as a RIS-PACS solution for hospitals. In the event that a received parameter used in monitoring and describing a particular service state, deviates from an expected parameter value, a watchdog system restarts the service or notifies a service (monitoring) worker of the deviation. Monitored parameters indicate service states including, for example, a service failed, a service is stopped or a service is running.

In contrast system 10 advantageously provides information about a variety of performance problems in an individual communication interface application. System 10 advantageously statistically evaluates typical performance of an individual interface application and determines if communication performance within an individual communication interface application is good, bad or dangerous. The system is usable in a variety of different communication systems and protocols including with DICOM communication, HL7 communication and other healthcare communication. In system 10, an individual communication interface application is advantageously responsible for monitoring its own communication performance and an individual interface application makes a decision to inform a monitoring server or to notify a client of variation in performance from normal. In another embodiment a server application advantageously monitors communication performance of multiple interface applications and gathers performance related data for statistical evaluation. This capability enables system 10 or an administrator to effectively and efficiently monitor DICOM interfaces, for example, so that they can quickly address problems before they adversely affect patient care.

Figure 2:
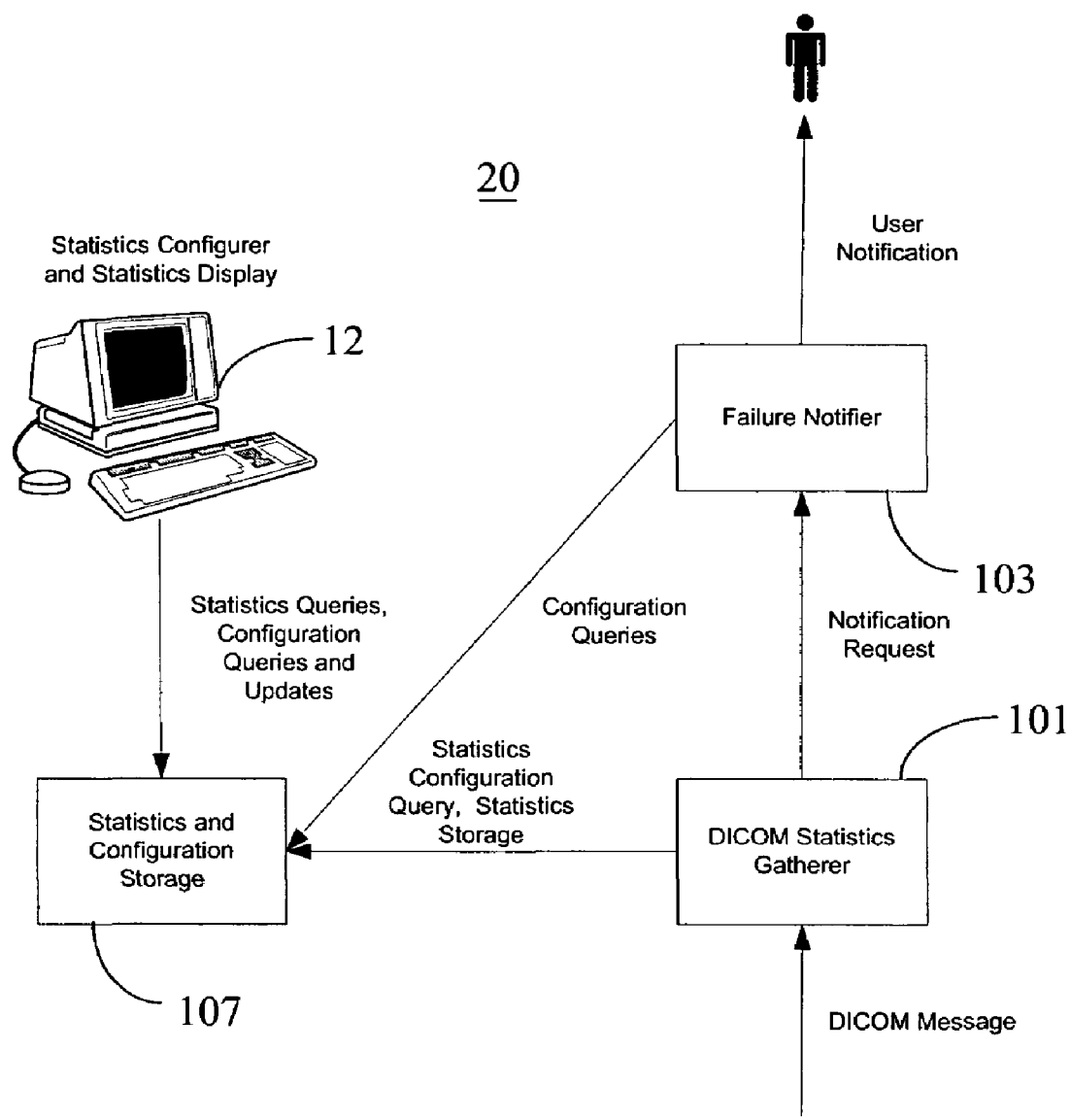
FIG. 2 shows a statistics processing system used in monitoring performance of a communication interface supporting communication of patient medical data, according to invention principles.

FIG. 2 shows a statistics processing system 20 used in monitoring performance of a communication interface supporting communication of patient medical data. Alternatively, the statistics processing system may be incorporated in other applications or units in system 10 (FIG. 1) or may be distributed among different units or applications in system 10. Units 101, 103 and 107 and workstation 12 implement statistic-based communication interface performance monitoring of healthcare communication protocol performance. The functions of units 101, 103 and 107 are partially implemented to operate on individual communication interface applications and are partially implemented to operate on a monitoring computer. DICOM Statistics Gatherer 101 collates statistics concerning performance of an individual communication interface between a local first Application Entity and a remote second Application Entity, in response to a message having a configured type being received on the individual communication interface. Statistics Gatherer 101 stores collated performance statistics for subsequent retrieval and access.

Failure Notifier 103 determines when a given performance statistic is determined by a preconfigured rule to exceed a performance range or error rate, for example and notifies healthcare workers via a predetermined method, such as via email, pager, voice etc. Failure Notifier 103 is configured to periodically survey performance statistics for a given communication interface and send notifications to healthcare workers as needed. Statistics Configuration unit 107 supports configuration of a given interface to record performance statistics concerning DICOM SOP Classes, for example. In response to preconfigured rules employed by Failure Notifier 103 indicating performance parameters of an individual communication interface exceed performance indication thresholds, notification messages are sent to healthcare workers. Also, Statistics Configuration unit 107 enables predetermination of communication means (e.g., email, pager, phone, voice mail) and associated conditions for triggering notification of a particular user of communication interface performance deviations from normal. Statistics Configuration unit 107 provides a graphical user interface (GUI) allowing display of system-wide DICOM performance statistics or performance statistics concerning a particular communication interface over a specified time period and also enables printing of reports. Unit 107 further stores performance statistics and configuration information internally or elsewhere in a network accessible location and responds to user initiated queries for statistics from workstation 12.

System 20 is employed in monitoring autonomous server based applications. Units 101, 103 and 107 may be incorporated in individual computers within a networked hospital system employing DICOM communication such as imaging Modality devices, a PACS system, a Radiology Information System (RIS), workstation Reporting station and communication server. In operation, Failure Notifier 103 sends a parameter to a monitoring server such as server 14 (FIG. 1) in response to detection of a statistically determined deviation of communication interface performance from a predetermined normal performance range. Monitoring server 14 receives a parameter from Failure Notifier 103 and attempts to repair a problem automatically (by restarting individual services on an interface application or by another method). If it is not possible to repair the problem automatically, Failure Notifier 103 communicates a message to a service worker identifying the problem.

In other embodiments a variety of combinations and distribution of units 101, 103 and 107 may occur within a distributed radiology information system and communication network, for example. The system advantageously collects performance and failure statistics for DICOM interfaces and initiates display of one or more images in response to user command providing graphical and other views of statistical performance data and other data for a user selected interface on client device 12 (FIG. 2). Units 101, 103 and 107 incorporate an application that collates communication interface performance statistics and stores them in a database. Units 101, 103 and 107 in system 10 (FIG. 1), employ derived communication interface statistics and user-definable rules in advantageously identifying impaired or sub-optimal operation of medical communications protocol e.g. DICOM, HL7, interfaces. Units 101, 103 and 107 in system 10 incorporate an application (or multiple applications or procedures) that collates statistics for individual types of DICOM and HL7 message and supports configuration of rules for identification of problems and specification of individuals to be notified. The application in units 101, 103 and 107 also displays graphically and textually the performance of an interface between two interface applications or set of similar interfaces.

Workstation 12 of system 10 provides a system administrator, for example, an image display presenting DICOM communication interface performance statistics in graphical or other form. The image display also presents product documentation that describes the capability to use DICOM performance statistics to support DICOM interfaces. Communication interface performance statistics displayed for a particular communication interface (node) application (an Application Entity) include DICOM SOP Class statistics and DICOM Association statistics. Communication interface performance statistics displayed for multiple (aggregate) Application Entities of a particular node include a number of any kind of DICOM messages in a given time frame and different types of DICOM messages conveyed per time frame. The displayed DICOM SOP Class performance statistics include, minimum, maximum and average time for processing of a DICOM Message Service Element (DIMSE) message for an SOP class, a last DIMSE message received for the SOP, frequency of DIMSE messages for an SOP class as well as number of success, failure, pending and warning responses.

Further, SOP specific performance statistics displayed by workstation 12 of system 10 include, frequency of SOP specific statuses and the presence or absence of specific attributes. Displayed statistics for SOP Classes using a DIMSE C-FIND query include, types of queries, duration for each type of query, maximum and average number of responses and the number of cancellations. Displayed statistics for SOP Classes using DIMSE C-STORE include, images (SOP Instances) of a given modality received, maximum, minimum and average time to store an individual image by modality device and a number of compressed images received. DICOM Association Statistics displayed by workstation 12 of system 10 include, a number of Association Requests, a number of Association Accepts and Rejects, a number of Association Releases, a number of Association Aborts, reasons for aborts and types of aborts.

Failure Notifier 103 sends a notification of impaired performance of a communication interface application to an individual or to a monitoring system. The notification is derived based on a comparison between a current performance of a communication interface application and an expected performance of the communication interface application derived from a statistical survey. Units 101, 103 and 107 in system 20 (FIG. 2) provide a regular update of performance statistics and may be customized for different architectural configurations. In one configuration, an individual communication interface application is responsible for updating statistic and monitoring performance deviation. The individual communication interface application sends a notification to an individual or to a monitoring server. In another configuration, an individual communication interface application sends current performance parameters to a monitoring server. The monitoring server is responsible for gathering the parameters from the communication interface application and evaluating the current performance against stored statistics for the communication interface application. HL7 statistics and messages for other types of messaging protocols are also recorded and analyzed.

Figure 3:
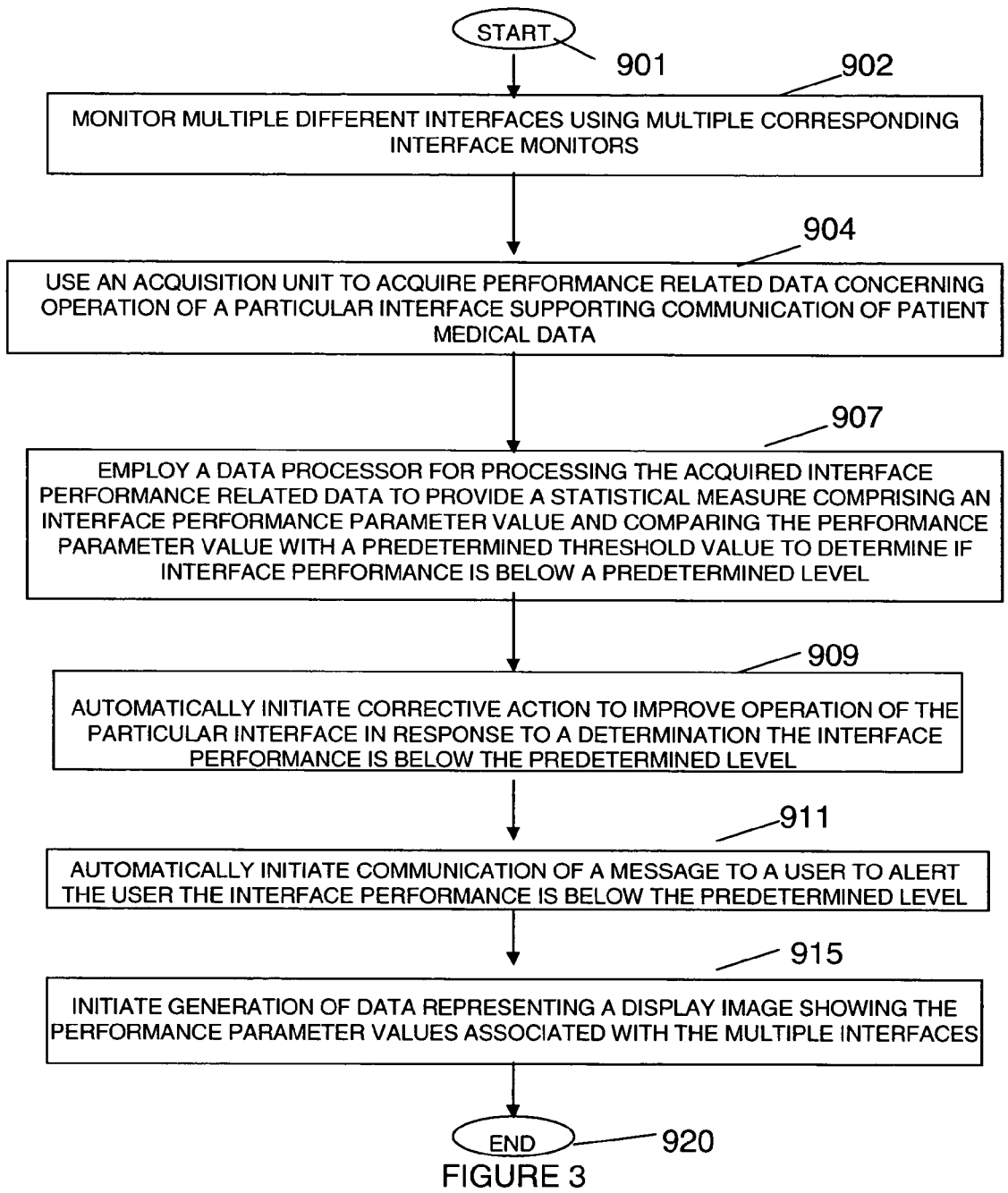
FIG. 3 shows a flowchart of a process employed in monitoring performance of a communication interface supporting communication of patient medical data, according to invention principles.

FIG. 3 shows a flowchart of a process employed by system 20 in monitoring performance of a communication interface comprising an executable application supporting interface operation and communication of patient medical data. The patient medical data comprises patient medical image representative data and patient specific data associated with a patient medical image. In step 902, following the start at step 901, multiple interface monitors in system 20 individually monitor corresponding multiple different interfaces. An individual interface monitor monitors (e.g., exclusively) a particular interface and includes an acquisition processor, a data processor and result processor. An acquisition processor in system 20 in step 904 acquires performance related data concerning operation of the particular interface supporting communication of patient medical data. The particular interface that supports communication of patient medical data is a DICOM protocol compatible interface or an HL7 (Health-Level 7) protocol compatible interface.

A data processor in system 20 in step 907 processes the acquired interface performance related data to provide a statistical measure comprising an interface performance parameter value and compares the performance parameter value with a predetermined threshold value to determine if interface performance is below a predetermined level. The performance related data comprises a Number of any kind of DICOM message conveyed in a given time frame and Types of DICOM messages per time frame. The performance related data also comprises DICOM SOP Class statistics or DICOM Association statistics. The DICOM SOP Class statistics include one or more of, (a) Minimum, maximum and average time for processing of a DIMSE message for the SOP, (b) Last DIMSE message received for the SOP, (c) Frequency of DIMSE messages for the SOP and (d) Number of success, failure, pending and warning responses. The DICOM SOP Class statistics include Frequency of SOP-specific statuses, Presence or Absence of specific attributes, Types of queries, Duration for each type of query, Maximum and average number of responses and Number of cancellations. The DICOM SOP Class statistics include for SOP Classes using DIMSE C-STORE, number of Images (SOP Instances) of a given modality received, Maximum, Minimum and Average time to store each image by modality, Number of compressed images received. Further, the DICOM Association Statistics include, Number of Association Requests, Number of Association Accepts and Rejects, Number of Association Releases, Number of Association Aborts, Reasons for aborts and Types of aborts.

A result processor in system 20 in step 909 automatically initiates corrective action to improve operation of the particular interface in response to a determination the interface performance is below the predetermined level. The result processor automatically initiates the corrective action to improve operation of the particular interface by restarting individual services provided by an application supporting the particular interface, re-initializing the application supporting the particular interface or initiating power reset to the particular interface. In response to the corrective action and a determination interface performance remains below a predetermined level, the result processor in step 911 automatically initiates communication of a message to a user to alert the user the interface performance is below the predetermined level.

A display processor in workstation 12 in system 20 in step 915 processes the statistical measure comprising a communication interface application performance parameter for presentation in a display image for viewing by a user. The display processor initiates generation of data representing a display image showing the performance parameter values associated with the corresponding plurality of interfaces. The process of FIG. 3 ends at step 920.

The systems and process presented herein are not exclusive. Other systems and processes may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. Further, any of the functions provided by the systems and process of FIGS. 1-3, may be implemented in hardware, software or a combination of both.

What is claimed is:

1. A system for monitoring performance of a communication interface supporting communication of patient medical data, comprising:

an acquisition unit for acquiring performance related data concerning operation of a particular interface supporting communication of patient medical data;

a data processor for processing said acquired interface performance related data to provide a statistical measure comprising an interface performance parameter value and comparing said performance parameter value with a predetermined threshold value to determine if interface performance is below a predetermined level; and a result processor for automatically initiating corrective action to improve operation of said particular interface in response to a determination said interface performance is below said predetermined level.

2. A system according to claim 1, wherein said particular interface supporting communication of patient medical data is at least one of, (a) a DICOM protocol compatible interface and (b) an HL7 (Health-Level 7) protocol compatible interface.

3. A system according to claim 1, wherein said result processor automatically initiates said corrective action to improve operation of said particular interface by at least one of, (a) restarting individual services provided by an application supporting said particular interface, (b) re-initializing said application supporting said particular interface and (c) initiating power reset to said particular interface.

4. A system according to claim 3, wherein in response to said corrective action and another determination interface performance remains below said predetermined level, said result processor automatically initiates communication of a message to a user to alert said user said interface performance is below said predetermined level.

5. A system according to claim 1, wherein said system exclusively monitors performance of said particular interface.

6. A system according to claim 1, wherein an interface comprises an executable application supporting interlace operation and communication of patient medical data.

7. A system according to claim 1, including a display processor for processing said statistical measure for presentation in a display image to a user.

8. A system according to claim 1, wherein said performance related data comprises at least one of, (a) DICOM SOP Class statistics and (b) DICOM Association statistics.

9. A system according to claim 8, wherein said DICOM SOP Class statistics include one or more of, (a) Minimum, maximum and average time for processing of a DIMSE message for the SOP, (b) Last DIMSE message received for the SOP, (c) Frequency of DIMSE messages for the SOP and (d) Number of success, failure, pending and warning responses.

10. A system according to claim 8, wherein said DICOM SOP Class statistics include one or more of, (a) Frequency of SOP-specific statuses, (b) Presence or Absence of specific attributes, (c) Types of queries, (d) Duration for each type of query, (e) Maximum and average number of responses and (f) Number of cancellations.

11. A system according to claim 8, wherein said DICOM SOP Class statistics include for SOP Classes using DIMSE C-STORE, one or more of, (a) number of Images (SOP Instances) of a given modality received, (b) Maximum, Minimum and Average time to store each image by modality, (c) Number of compressed images received.

12. A system according to claim 8, wherein said DICOM Association Statistics include one or more of, (a) Number Association Requests, (b) Number of Association Accepts and Rejects, (c) Number of Association Releases, (d) Number of Association Aborts, (f) Reasons for aborts and (g) Types of aborts.

13. A system according to claim 1, wherein said performance related data comprises at least one of, (a) Number of any kind of DICOM message conveyed in a given time frame and (b) Types of DICOM messages per time frame.

14. A system according to claim 1, wherein said patient medical data comprises at least one of, (a) patient medical image representative data and (b) patient specific data associated with a patient medical image.

15. A system for monitoring performance of DICOM compatible communication interfaces supporting communication of patient medical data, comprising:
a plurality of interface monitors for individually monitoring a corresponding plurality of different interfaces and an individual interface monitor for monitoring a particular interface comprises,
an acquisition unit for acquiring performance related data concerning operation of a particular interface supporting communication of patient medical data;
a data processor for processing said acquired interface performance related data to provide a statistical measure comprising an interface performance parameter value and comparing said performance parameter value with a predetermined threshold value to determine if interface performance is below a predetermined level; and
a result processor for automatically initiating corrective action to improve operation of said particular interface in response to a determination said interface performance is below said predetermined level.

16. A system for centralized monitoring performance of communication interfaces supporting communication of patient medical data, comprising:
an acquisition unit for acquiring performance related data concerning operation of a plurality of interfaces supporting communication of patient medical data;
a data processor for processing said acquired interface performance related data for said plurality of interfaces to provide statistical measures comprising interface performance parameter values and comparing said performance parameter values with predetermined threshold values to determine if interface performance is below a predetermined level;
a result processor for automatically initiating corrective action to improve operation of a particular interface in response to a determination performance of said particular interface is below said predetermined level; and
a display processor for initiating generation of data representing a display image showing said performance parameter values associated with said corresponding plurality of interfaces.

17. A system for monitoring performance of a communication interface supporting communication of patient medical data, comprising:
an acquisition unit for acquiring performance related data concerning operation of a particular interface supporting communication of patient medical data;
a data processor for processing said acquired interface performance related data to provide a statistical measure comprising an interface performance parameter value and comparing said performance parameter value with a predetermined threshold value to determine if interface performance is below a predetermined level; and
a result processor for automatically initiating corrective action to improve operation of a particular interface in response to a determination performance of said particular interface is below said predetermined level and automatically initiating communication of a message to a user to alert said user said interface performance is below said predetermined level.

* * * * *